United States Patent [19]

Claude

[11] Patent Number: 4,982,742
[45] Date of Patent: Jan. 8, 1991

[54] APPARATUS AND METHOD TO FACILITATE HEALING OF SOFT TISSUE WOUNDS

[75] Inventor: John P. Claude, Redwood City, Calif.

[73] Assignee: C&Y Technology, Inc., Palo Alto, Calif.

[21] Appl. No.: 313,981

[22] Filed: Feb. 22, 1989

[51] Int. Cl.$^5$ ............................................. A61N 1/18
[52] U.S. Cl. .................................. 128/798; 128/82.1; 128/422
[58] Field of Search ............... 128/783, 798, 802, 803, 128/82.1, 419 F, 421, 422

[56] References Cited

U.S. PATENT DOCUMENTS

| | | | |
|---|---|---|---|
| 3,472,233 | 10/1969 | Sarbacher | 128/422 |
| 3,888,261 | 6/1975 | Maurer | 128/421 |
| 4,092,464 | 5/1978 | Dey et al. | 429/127 |
| 4,142,521 | 3/1979 | Konikoff | 128/82.1 |
| 4,177,819 | 12/1979 | Kofsky et al. | 128/422 |
| 4,266,532 | 5/1981 | Ryaby et al. | 128/1.5 |
| 4,315,503 | 2/1982 | Ryaby et al. | 128/1.5 |
| 4,398,545 | 8/1983 | Wilson | 128/798 |
| 4,456,001 | 6/1984 | Pescatore | 128/1.5 |
| 4,550,714 | 11/1985 | Talish et al. | 128/1.5 |
| 4,556,055 | 12/1985 | Bonner, Jr. | 128/82.1 |
| 4,574,809 | 3/1986 | Talish et al. | 128/419 |
| 4,614,179 | 9/1986 | Gardner et al. | 128/64 |
| 4,614,180 | 9/1986 | Gardner et al. | 128/64 |
| 4,616,629 | 10/1986 | Moore | 128/1.5 |
| 4,619,252 | 10/1986 | Ibbott | 128/82.1 |
| 4,620,543 | 11/1986 | Heppenstall et al. | 128/419 F |
| 4,696,289 | 9/1987 | Gardner et al. | 128/64 |
| 4,702,232 | 10/1987 | Gardner et al. | 128/64 |
| 4,721,101 | 1/1988 | Gardner et al. | 128/64 |
| 4,725,263 | 2/1988 | McNichols et al. | 604/20 |
| 4,731,926 | 3/1988 | Sibalis | 29/877 |

FOREIGN PATENT DOCUMENTS 2148717  6/1985  United Kingdom ...................... 1/34

OTHER PUBLICATIONS

"Accelerated Healing of Skin Ulcers by Electrotherapy: Preliminary Clinical Results", Woolcott et al., Southern Medical Journal, (Jul. 1969).
"Electrical Promotion of Soft Tissue Repairs", J. J. Konikoff, (Aug. 1975).
"Wound Healing Promotion by the Use of Negative Electric Current", D. Assimacopoulos, The American Surgeon, vol. 36, No. 6, (Jun. 1986).
"Electric Bandages Heal Wounds Quicker", San Jose Mercury News, (Aug. 26, 1988).
"Diapulse Corp. of America Reduces Swelling Electromagnetically", Ground Floor, vol. 7, No. 10, (Jun. 10, 1988).
"This Bandage Gives Wounds a Healing Jolt" (publication unknown).
"Staodyn" Report dated Feb. 9, 1988.

*Primary Examiner*—Lee S. Cohen
*Assistant Examiner*—S. Getzow
*Attorney, Agent, or Firm*—Flehr, Hohbach, Test, Albritton & Herbert

[57] ABSTRACT

A method and an apparatus for facilitating the healing of soft tissue wounds. The method includes the steps of selecting an area of tissue that is wounded, and applying therapeutic microcurrent excursions ranging from 100 to 1,000 microamperes and having a frequency of 10 to 50 hertz to the selected area of tissue. The apparatus includes a bandage containing circuitry for generating the therapeutic microcurrent excursions and a first and a second electrode coupled to the circuitry. A housing holds said first and second electrodes apart and adjacent to said selected area of tissue when the apparatus is placed over the selected area of tissue. During operation of the apparatus, an electric circuit is completed as microcurrent excursions propagate from the first electrode across the selected tissue wound to the second electrode.

17 Claims, 2 Drawing Sheets

APPARATUS AND METHOD TO FACILITATE HEALING OF SOFT TISSUE WOUNDS

The present invention relates generally to an apparatus and method for facilitating the healing of soft tissue wounds, and more particularly to a bandage capable of generating and applying microcurrents excursions across a soft tissue wound.

BACKGROUND OF THE INVENTION

Applying therapeutic electro-stimulation to various parts of the body is known. See for example U.S. Pat. Nos. 4,619,252 issued to Ibott, 4,556,055 issued to Bonner Jr, 4,315,503 and 4,266,532 issued to Ryaby et al, and 4,142,521 issued to Konikoff. However, the prior art does not provide a disposable bandage capable of generating and applying microcurrent excursions across a soft tissue wound, nor does the prior art provide such a bandage in a self contained package which keeps the bandage sterile and protects the internal battery from discharging before use.

SUMMARY OF THE INVENTION

Accordingly, it is a primary objective of the present invention to provide an apparatus and a method to facilitate the healing of soft tissue wounds utilizing microcurrent excursions.

Another object of the invention is to provide a sterile, disposable bandage containing an integrated circuit and a power source to generate the microcurrent excursions.

Another object of the invention is to provide a bandage for facilitating the healing of soft tissue wounds by applying microcurrent excursions ranging in amplitude from 100 to 1000 microamperes at a frequency of 10 to 50 hertz and having a net voltage of approximately zero volts to the affected tissue.

To achieve the foregoing and other objects and in accordance with the purpose of the present invention, there is provided a method and an apparatus for facilitating the healing of soft tissue wounds. The method includes the steps of selecting an area of tissue that is wounded, and applying therapeutic microcurrent excursions ranging from 100 to 1,000 microamperes and having a frequency of 10 to 50 hertz to the selected area of tissue. The apparatus includes a bandage containing circuitry for generating the therapeutic microcurrent excursions and a first and a second electrode means coupled to the circuitry. A housing holds the first and second electrode means apart and adjacent to the selected area of tissue when the apparatus is placed over the selected area of tissue. During operation of the apparatus, an electric circuit is completed as microcurrent excursions propagate from the first electrode means across the selected tissue wound to the second electrode means.

BRIEF DESCRIPTION OF THE DRAWINGS

Additional objects and features of the invention will be more readily apparent from the following detailed description and appended claims when taken in conjunction with the drawings, in which:

DESCRIPTION OF THE PREFERRED EMBODIMENT

Figure 1:
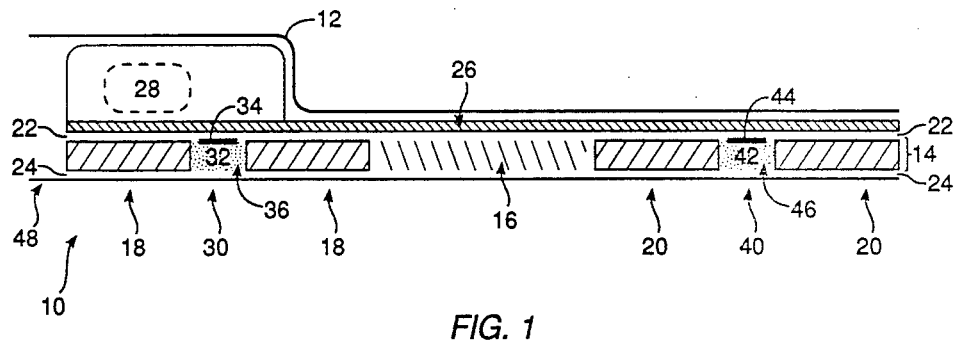
FIG. 1 is a side view of the apparatus incorporating the present invention and particularly showing a top overlay layer, a flexible circuit strip, and a bandage base.

Reference is initially made to FIG. 1, which shows a side view of the apparatus 10 according to the present invention. The apparatus 10 comprises a bandage having a top overlay layer 12, and a bandage base 14. The bandage base 14 includes a gauze portion 16 and two pads 18 and 20 located on either side of the gauze portion 16. Each pad has a sticky adhesive top surface 22 and a sticky adhesive bottom surface 24. A flexible circuit strip 26 containing circuitry 28 for generating microcurrent excursions is sandwiched between the overlay layer 12 and the base 14. The flexible circuit strip 26 and the top overlay 12 are adapted to adhere the adhesive top surfaces 22 of pads 18 and 20 respectively to form the three layered bandage 10.

The first pad 18 contains a well-like perforated housing 30 for mechanically coupling or holding a first electrode means 32. The first electrode means 32 includes a positive electrode 34 positioned in the upper region of the perforated housing proximate the flexible circuit strip 26 and is electrically coupled to the circuit 28. The electrode means also includes a layer of conductive gel 36 electrically coupled to the bottom of electrode 34 and extends the depth of the well 30 to the bottom surface 24 of pad 18. Hence, during use of the bandage 10 when it is coupled to a selected area of tissue, the gel 36 is in contact with the tissue and is capable of conducting microcurrent excursions generated by the circuit 28 to the tissue.

The second pad 20 contains a second well-like housing 40 for mechanically coupling or holding a second electrode means 42. The second electrode means 42 includes a negative electrode 44 mechanically positioned in the upper region of the perforated housing proximate the flexible circuit strip 26 and is electrically coupled to a ground point on circuit 28. The second electrode means 42 also includes a second layer of conductive gel 46 electrically coupled to the bottom of electrode 44 and extends the depth of the well 40 to the bottom surface 24 of pad 20. Hence, during use of the bandage 10 when it is coupled to a selected area of tissue, the gel 46 is in contact with the tissue and is capable of conducting microcurrent excursions originating from the first electrode means 32 and propagating through the selected tissue to negative electrode 44 and ground point to complete an electronic circuit.

To protect the bandage 10 from contamination and the like prior to application to a wound, a sterile plastic peel strip 48 is affixed across the bottom surfaces 24 of pads 18, 20 and the gauze portion 16. Once the flexible strip 48 is peeled away to expose the sticky bottom surfaces 24 of pads 18 and 20, respectively, bandage 10 is adhered to a selected area of tissue having a wound.

Figure 2:
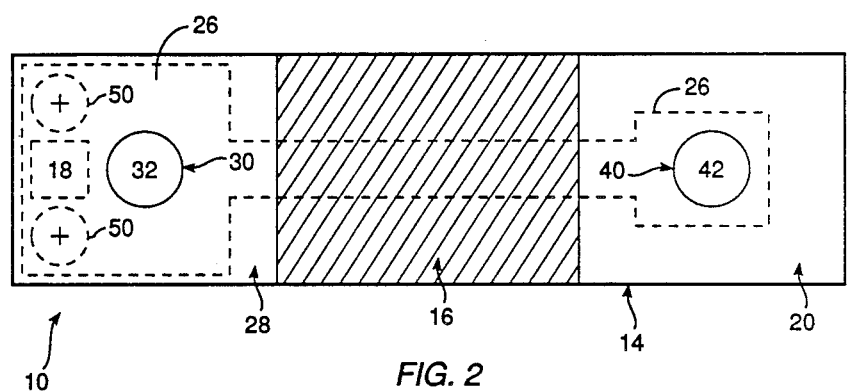
FIG. 2 is a bottom view of the apparatus shown in FIG. 1 and particularly showing the bandage base and the flexible circuit strip according to the present invention.

Referring now to FIG. 2, a bottom view of the apparatus particularly showing the bandage base 14 and circuit strip 26 with the peel strip 48 removed is shown. The bandage base 14 including pads 18 and 20 respectively positioned on opposite sides of the gauze 16. The location of housings 30 and 40 in pads 18 and pads 20 respectively position the electrode means 32 and 42 apart and adjacent the selected area of tissue having a wound. The circuit strip 26, illustrated by broken lines, extends from pad 18 across the gauze portion 16 to pad 20. The circuit strip 26 includes a electronic circuit 28 for generating the therapeutic microcurrents, a power source 50 to energize circuit 28 and the electrodes means 32 and 42.

Figure 3:
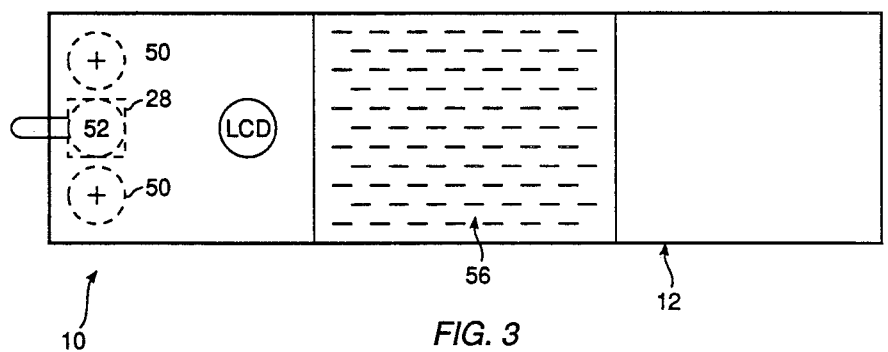
FIG. 3 is a top view of the apparatus shown in FIG. 1 and particularly showing the top overlay layer according to the present invention.

Referring now to FIG. 3, a top view of the apparatus particularly showing the features on the top overlay layer according to the present invention is shown. The top layer 12 is a flesh colored plastic overlay strip with a sticky adhesive underside lining. The sticky underside lining of layer 12 along with the top adhesive surfaces 22 of pads 18 and 20 serve to bind the three layered bandage 10 together. The overlay 12 covers the flexible circuit 26 and provides a protective sterilized shield for the pads 18, 20 and gauze 16 resting over the underlying wound. The portion of the overlay 12 resting above the gauze 16 has a multiplicity of tiny perforations 54 to permit air circulation to reach the wounded tissue under the gauze. An indicating LCD device is located on the top surface of the overlay 12 to provide a visual means when lit to inform the patient that the power source 50 is sufficient to drive circuit 28 to generate the therapeutic microcurrent excursions. It will be appreciated by those skilled in the art that the LCD may be replaced with any indicating means, including, but not limited to an LED device. A pull away tab 52 is electro-mechanically connected between the power source 50 and ground point on circuit 28. When the pull away tab 52 is intact, the power source 50 is connected to ground point and energization of the circuit 28 does not occur. Once the pull away tab is removed, the electrical connection between the power source 50 to ground is broken, and as result, the power source 50 drives the circuit 28 to generate the therapeutic microcurrent excursions.

Figure 4:
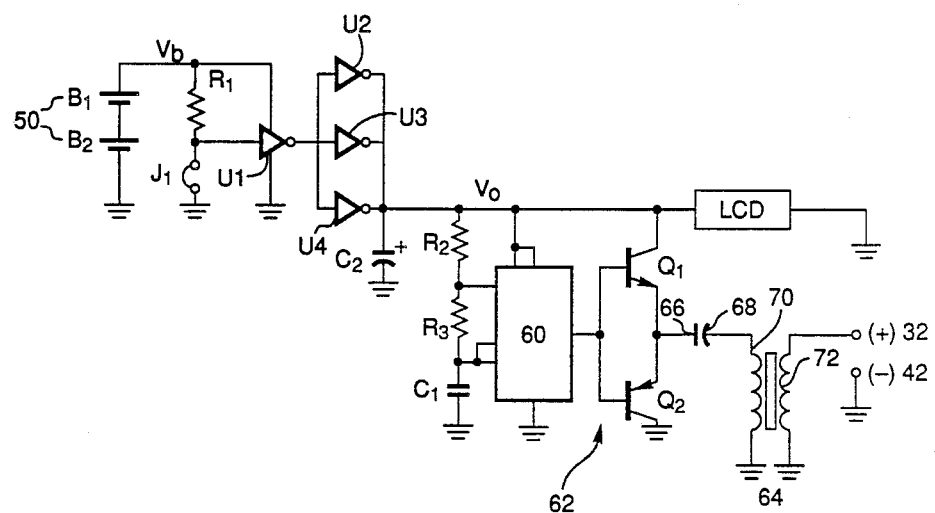
FIG. 4 is a diagram of the circuitry on the flexible circuit strip in the apparatus shown in FIGS. 1 and 2 for generating therapeutic microcurrents according to the present invention.

Referring to FIG. 4, a diagram of the circuit 28 for generating therapeutic microcurrents according to the present invention is shown. The major components of the circuit 28 include the power source 50 for generating a voltage Vb, an electrical jumper J1 electro-mechanically connected to the pull away tab 52 for selectively powering the remaining portion of circuit 28, a plurality of invertors (U1 through U4) for generating an oscillator input voltage Vo, an oscillator 60, a current amplifier 62, a transformer 64 for generating the microcurrent excursions and the electrodes means 32 and 42.

The power source 50 includes two light weight batteries B1 and B2 connected in series to provide a battery voltage Vb. When the perforated tab 52 is intact, a resistor R1 and J1 are connected in series between the Vb and ground. In the preferred embodiment, R1 is of high impedance to reduce the current flow between Vb and ground, thus significantly increasing the shelf life of batteries B1 and B2.

The input into invertor U1 is electrically coupled between R1 and J1. When the tab 52 is removed, breaking J1's electrical connection between Vb to ground, R1 pulls the current input into U1 from a low to a high. Consequently, the output of U1 is low. The three parallel invertors U2–U4 are electrically coupled to receive the low output of U1 and invert it into a voltage Vo. The output of the three invertors U2–U4 are tied together in parallel in order to provide adequate current supply compliance to drive the remaining portion of the circuit including oscillator 60, current amplifier 62, and transformer 64.

A CMOS oscillator 60 manufactured by Intersil is electrically connected to receive Vo and is adapted to generate in response thereto a series of positive square wave pulses with an amplitude of Vb and a frequency ranging from 10 to 50 hertz. The timing and amplitude characteristics of oscillator's 60 output are determined by resistors R2 and R3 and capacitor C1 connected to oscillator 60 in accordance to the manufacturer's specifications. Capacitor C2, electrically coupled between the invertors U2–U4 output and oscillator 60, acts to stabilize Vo during periods of peak current demand by oscillator 60.

A current amplifier 62, comprised of two transistors Q1 and Q2, is electrically connected to the output of the oscillator 60. The square wave pulses are received at the bases of transistors Q1 and Q2. A capacitor C3 having a first plate 66 and a second plate 68 and the transformer 64 having a primary coil 70 and a secondary coil 72 are electrically connected in series to the emitter outputs of the two transistors Q1 and Q2. The emitter outputs of transistors Q1 and Q2 alternately charge and discharge capacitor C3's first plate 66 in response to the AC components of the square wave pulse output of oscillator 60. Capacitor C3's second plate 68 is consequently charged and discharged through the primary coil 70 of transformer 64. The charging and discharging of currents in the primary coil 70 induces the bi-phase microcurrent excursions in the transformer's secondary coil 72. The output of the secondary coil 72 is electrically connected to the positive electrode means 32. Thereafter, the current excursions propagate across the selected tissue between the first electrode means 32 to the second electrode means 42 and then to ground. In this manner, the therapeutic microcurrent excursions illustrated in FIG. 5 are applied to the selected area of skin having a wound.

Vo is also electrically connected to drive the LCD located on the overlay 12. The LCD has a minimum operational threshold voltage which corresponds to the minimum voltage required to drive circuit 28 to generate the therapeutic microcurrent excursions. When Vo falls below the threshold, the LCD is turned off indicating the bandage 10 is in need of replacement.

Figure 5:
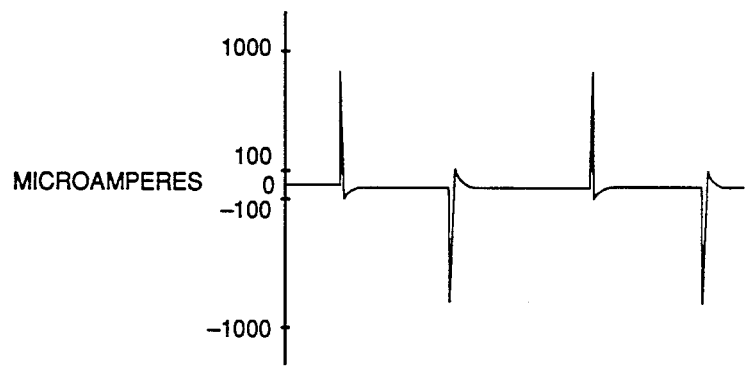
FIG. 5 is a graph showing the therapeutic microcurrent excursions generated by the circuitry of FIG. 4 and applied to the selected area of tissue having a wound according to the present invention.

Referring now to FIG. 5, a diagram showing the therapeutic microcurrent excursions generated by the circuitry of FIG. 4 is shown. The bi-phase waveform is characterized by a frequency ranging from 10 to 50 hertz and an amplitude ranging between 100 and 1000 microamps. The waveform is further characterized by a net voltage of approximately zero volts. In the preferred embodiment, it has found that microcurrent excursions having an amplitude range of 100 to 500 microamperes is most effective in facilitating the healing of soft tissue wounds.

To properly employ the bandage 10 to a selected area of tissue having a wound, the sterile peel strip 48 is first removed to expose the bottom adhesive surfaces 24 of pads 18 and 20. The bandage is then adhered to the selected area of tissue. Care should be taken to ensure that the wound is fully covered by the gauze portion 16, and that electrode means 32 and 42 are on opposite sides of the wound. Removal of the pull away tab 52 results in the energization of circuit 28 and therefore the generation and application of therapeutic microcurrent excursions ranging from 50 to 1,000 microamperes and having a frequency of 10 to 50 hertz to the wound. Accordingly, an electric circuit to facilitate soft tissue healing is completed as the microcurrent excursions propagate from said first electrode means 32 across the wound to the second electrode means 42. While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. Apparatus for facilitating the healing of soft tissue wounds, comprising:
    circuitry means for generating therapeutic microcurrent excursions;
    first and second electrode means coupled to said circuitry means for supplying the microcurrent excursions to a selected area of tissue between said first and second electrode means;
    housing means coupled to said first and second electrode means for holding said first and second electrode means apart and adjacent to said selected area of tissue;
    a three layered bandage;
    a sterile plastic overlay forming a top layer of the bandage;
    a flexible circuit strip containing said circuitry means and said first and second electrode means, said flexible circuit strip forming a middle layer of the bandage and situated beneath said top layer; and
    bandage base means containing said housing means for holding said first and second electrode means apart, and having a gauze portion adapted to be placed over the selected area of tissue, and adhesive pad means adapted to couple the apparatus to said selected area of tissue, said bandage base means situated beneath said middle layer to form a bottom layer of the bandage;
    whereby an electric circuit is completed as microcurrent excursions propagate from said first electrode means across the selected area of tissue to the second electrode means to facilitate healing of the soft tissue wound.

2. The apparatus of claim 1, wherein the said circuitry means generates microcurrent excursions ranging from 50 to 1,000 microamperes and having a frequency of 10 to 50 hertz.

3. The apparatus of claim 1, wherein said bandage base means includes perforations to house said first and second electrode means, said perforations positioning said electrode means adjacent said selected area of tissue.

4. The apparatus of claim 3, wherein each said electrode means further comprises a conductive electrode electrically coupled to said circuitry means and a layer of sterile conductive gel for coupling said conductive electrode to said selected area of tissue.

5. The apparatus of claim 1, wherein said flexible circuit strip is positioned between said sterile plastic overlay and said bandage base means.

6. The apparatus of claim 1, including a power source and a pull-away tab means for coupling said circuitry means to said power source when said pull-away tab means is removed, whereby removal of said pull-away tab causes said power source to energize said circuitry means resulting in the generation of the therapeutic microcurrents.

7. The apparatus of claim 6, wherein said circuitry means further includes power indicating means electrically coupled to said power source for providing a visible indication of the sufficiency of said power source for generating therapeutic microcurrents.

8. The apparatus of claim 1, wherein said circuitry means comprises a power source for producing a steady voltage, oscillator means electrically coupled to said power source for generating pulses at a frequency ranging between 10 to 50 hertz, and transformer means coupled to said oscillator means for generating microcurrent excursions.

9. The apparatus of claim 1 wherein said therapeutic microcurrent excursions maintain a net voltage of approximately zero volts.

10. The apparatus of claim 3 wherein said adhesive pad means comprises two adhesive pads.

11. A method for healing soft tissue wounds utilizing microcurrent excursions, comprising the steps of:
    selecting a area of tissue having a soft tissue wound; and
    applying therapeutic microcurrent excursions ranging from 50 to 1,000 microamperes and having a frequency of 10 to 50 hertz to said selected area of tissue having a soft tissue wound in order to facilitate the healing of said soft tissue wound.

12. The method of claim 11, wherein said step of applying therapeutic microcurrent excursions further includes the step of:
    adhering a disposable, sterile bandage containing circuitry means capable of generating said therapeutic microcurrent excursions to said selected area of tissue; said sterile bandage having first and second electrode means for coupling said circuitry means to said selected area of tissue;
    whereby an electric circuit is completed as microcurrent excursions propagate from said first electrode means across the selected area of tissue to the second electrode means to facilitate healing of the tissue.

13. The method of claim 11 wherein said therapeutic microcurrent excursions maintain a net voltage of approximately zero volts.

14. A bandage for facilitating the healing of soft tissue wounds, comprising:
    a flexible circuit strip containing circuitry means for generating therapeutic microcurrent excursions, and first and second electrode means coupled to said circuitry means for supplying said microcurrent excursions to a selected area of tissue placed between said first and second electrode means;
    a sterile plastic overlay covering the flexible circuit strip;
    bandage base means having a gauze portion adapted to be placed over the selected area of tissue, and an adhesive pad means adapted to couple said bandage to said selected area of tissue, said bandage base means coupled to and situated below said flexible circuit strip;
    whereby an electric circuit is completed as microcurrent excursions propagate from said first electrode means across the selected area of tissue to the second electrode means to facilitate healing of soft tissue wounds in the selected area of tissue.

15. The bandage of claim 14, wherein the said circuitry means generates microcurrent excursions ranging from 50 to 1,000 microamperes and having a frequency of 10 to 50 hertz.

16. The bandage of claim 14, wherein said bandage base means includes perforations to house said first and second electrode means, said perforation positioning said electrode means adjacent said selected area of tissue.

17. The bandage of claim 16, wherein each said electrode means further comprises conductive electrode means electrically coupled to said circuitry means and a layer of sterile conductive gel for coupling said conductive electrode means to said selected area of tissue.

* * * * *